United States Patent [19]

Gaudet et al.

[11] Patent Number: 4,826,678
[45] Date of Patent: May 2, 1989

[54] FATTY ACID SALT ENHANCEMENT OF BACTERIAL INSECTICIDE

[75] Inventors: Michelle D. Gaudet, Victoria; George S. Puritch, Brentwood Bay, both of Canada

[73] Assignee: Safer, Inc., Newton, Mass.

[21] Appl. No.: 180,684

[22] Filed: Apr. 8, 1988

Related U.S. Application Data

[63] Continuation of Ser. No. 78,012, Jun. 24, 1987, abandoned, which is a continuation of Ser. No. 885,679, Jul. 15, 1986, abandoned, which is a continuation-in-part of Ser. No. 722,459, Jun. 12, 1985, abandoned.

[51] Int. Cl.$^4$ ............................................. A01N 63/00
[52] U.S. Cl. ...................................................... 424/93
[58] Field of Search .......................................... 424/93

[56] References Cited

U.S. PATENT DOCUMENTS

| | | |
|---|---|---|
| 3,087,865 | 4/1963 | Drake . |
| 3,113,066 | 12/1963 | Edmond . |
| 3,911,110 | 10/1975 | Smirnoff . |
| 3,937,813 | 2/1976 | Clark, Jr. . |
| 3,944,664 | 3/1976 | Kitagaki et al. . |
| 4,107,294 | 8/1978 | Chauthani . |
| 4,467,036 | 8/1984 | Schnepf et al. . |

FOREIGN PATENT DOCUMENTS

1084001  4/1984  U.S.S.R. ................................ 424/93

OTHER PUBLICATIONS

Kreeg, A., and Langenbruck, G. A., "Susceptibility of Arthropod Species to *Bacillus thuringiensis*", in Microbial Control of Pests and Plant Diseases, Burgess, H. D., ed., Premium Press, N.Y., pp. 836–836 (1970–1980).

Falson, L. A., "Microbial Control as a Tool in Integrated Control Programs", pp. 346–364 (1971).
Jacques, R. P., "The Potential of Pathogens for Pest Control", pp. 101–126 (1983).
Stanford Research Institute Study (1977), "New Innovative Pesticides: An Evaluation of Incentives and Disincentives for Commercial Development by Industry, prepared for United States Environmental Protection Agency, Office of Pesticide Programs", pp. 47–113 (1977).
Puritch, G. S., "Biocidal Effects of Fatty Acid Salts on Various Forest Insect Pests", pp. 105–112 (1978).
Couch, T. L. and Ignoffo, C. M., "Formulation of Insect Pathogens", Chapter 34, pp. 621–634 (1981).
Jaques, R. P. and Morris, O. N., "Compatability of Pathogens with Other Methods of Pest Control and with Different Crops", Chapter 38, pp. 695–715 (1981).

*Primary Examiner*—Shep K. Rose
*Attorney, Agent, or Firm*—Lahive & Cockfield

[57] ABSTRACT

The activity of the microbial insecticide, *Bacillus thuringiensis* (B.t.) Berliner has been found to be synergistically enhanced by the addition of unsaturated 18-carbon fatty acid salts. A synergistic effect with respect to increased larval mortality of the western spruce budworm, *Choristoncura occidentalis* Freeman was obtained in the $C_{18}$ unsaturated fatty acid/B.t. treatments. Enhanced mortality was also observed in $C_{18}$ fatty acid/B.t. treatments of the larval form of the silverspotted tiger moth, *Halisidota argentata* Packard. The increased insecticidal activity of the entomogenous bacteria, *Bacillus thuringiensis* (B.t.) Berliner by the addition of unsaturated 18-carbon fatty acids represents a significant breakthrough for the expanded use of this microbial insecticide.

26 Claims, No Drawings

FATTY ACID SALT ENHANCEMENT OF BACTERIAL INSECTICIDE

REFERENCE TO RELATED APPLICATIONS

This application is a continuation of copending U.S. application Ser. No. 078,012, filed July 24, 1987, which was a continuation of application Ser. No. 885,679, filed July 15, 1986, which was a continuation in part of application Ser. No. 722,459 filed June 12, 1985, all entitled Fatty Acid Salt Enhancement of Bacterial Insecticides, and all now abandoned.

FIELD OF INVENTION

This invention is concerned with the synergistic enhancement of the microbial insecticide, *Bacillus thuringiensis* (B.t.) Berliner by the addition of unsaturated 18-carbon fatty acid soaps.

INFORMATION DISCLOSURE STATEMENT

Dissatisfaction with the dependence on chemical insecticides for protection of crops against pest insects has led to more serious consideration of biological agents for the regulation of insects. Along with the exploitation of parasitic and predaceous species of arthropods, the utility of disease producing microorganisms as an alternate method for insect control is well documented.

Since its first appearance to the United States market in 1958 (L. A. Falcon, 1971 Microbial control as a tool in integrated control programs in Biological Control. C. B. Huffaker (ed.) Plenum Press, London and New York, pp. 346-362), many commercial preparations containing *Bacillus thuringiensis* (B.t.) have become available worldwide for the control of various lepidopterous and dipterous pests. The use of B.t. is attractive for management of pest insects because it is specific for target insects with little or no adverse impact on the beneficial or non-target arthropod fauna and is not hazardous to humans, mammals or other important animals. As a naturally occurring insect pathogen, B.t. does not pollute the field habitat and insect pests are not as likely to develop resistance or tolerance to it (R. P. Jaques, 1983 The potential of pathogens for pest control. Agric., Ecosystems and Environ., Vol. 10: pp. 101-126). The two major obstacles to greater use of B.t., as cited in the Stanford Research Institute Study (1977 New innovative pesticides: an evaluation of incentives and disincentives for commercial development by industry, prepared for United States Environmental Protection Agency, Office of Pesticide Programs, pp. 174), are low or variable efficacy of control and high cost of product.

Research has shown that the unsaturated $C_{18}$ fatty acids or their salts ($C_{18:x}$) are highly toxic to soft bodied insects including adelgids, aphids, mealybugs, whitefly, pear psylla, rose slugs, etc. (G. S. Puritch 1978 Symposium on the pharmacological effects of lipids. AOCS monograph No. 5, 105-112).

Various attempts have been made in order to improve the B.t. based insecticide composition. U.S. Pat. No. 3,113,066 to Emond teaches use of a pesticidal oil in combination with B.t. U.S. Pat. No. 3,911,110 to Smirnoff teaches the concurrent use of the enzyme chitinase and B.t. U.S. Pat. No. 3,937,813 to Clark, Jr. discloses a composition containing B.t. and N'-(4-chloro-o-tolyl)-N,N-dimethyl formamidine, U.S. Pat. No. 3,944,664 to Kitagaki et al describes a synergistic acaricidal composition comprising the toxin of B.t. and an acaricide selected from 1,1-bis(p-chlorophenyl)ethanol, bis-(p-chlorophenyl)sulfide and bis(p-chlorophenoxy)methane. U.S. Pat. No. 4,107,294 to Chauthani teaches the combination of B.t. and 1-(4-chlorophenyl)-3-(2,6-difluorobenzoyl)-urea.

SUMMARY OF THE INVENTION

During recent investigations, it has been further discovered that combinations of the unsaturated 18-carbon fatty acid salts were synergistic with respect to insecticidal activity in combination with various formulations of *Bacillus thuringiensis* Berliner. This unique finding provides a solution to one of the major obstacles to the expanded use of B.t.; that of low or variable efficacy. By increasing the efficacy of insect control with the addition of a $C_{18}$ unsaturated fatty acid salt synergist it may also be possible to reduce the amount of B.t. needed for control and reduce the product cost. Therefore, this finding represents a significant breakthrough for the expanded use of the microbial insecticide, *Bacillus thuringiensis* (B.t.) Berliner.

The invention thus provides an insecticidal composition consisting essentially of: (a) an insecticidally effective amount of an entomopathogenic bacterium *Bacillus thuringiensis* (B.t.) Berliner which is insecticidally active against sucking biting and defoliating insects, and (b) sodium, potassium or ammonium salt of an unsaturated fatty acid having 18 carbon atoms selected from the group consisting of oleic acid, linoleic acid and a mixture thereof in an amount sufficient to be insecticidally effective as well as to synergistically enhance the efficacy of the microbial insecticide, wherein the weight ratio of (a) B.t. (active ingredient): (b) the fatty acid salt is from about 1:1,000 to about 1:1.

The invention also provides a method of protecting susceptible plants and animals against biting, sucking and defoliating insects, which method comprises concurrently applying to the insects or habitat thereof both (a) an insecticidally effective amount of an entomopathogenic bacterium *Bacillus thuringiensis* (B.t.) Berliner which is insecticidally active against sucking, biting and defoliating insects and (b) sodium, potassium or ammonium salt of an unsaturated fatty acid having 18-carbon atoms selected from the group consisting of oleic acid, linoleic acid and a mixture thereof in an amount sufficient to be insecticidally effective as well as to synergistically enhance the efficacy of the microbial insecticide, wherein the weight ratio of (a) B.t. (active ingredient): (b) the fatty acid salt is from about 1:1,000 to about 1:1.

DETAILED DESCRIPTION OF INVENTION

The microbial insecticide (a) employed according to the present invention is an entomopathogenic bacterium *Bacillus thuringiensis* (B.t.) Berliner which is insecticidally active against sucking, biting and defoliating insects. The microorganisms *Bacillus thuringiensis* form protein-containing parasporal endotoxin crystals. The entomopathogenic nature of *Bacillus thuringiensis* is mainly to be attributed to the effect of endotoxin. It is known, however, that some strains of *Bacillus thuringiensis* produce an extracellular water soluble exotoxin in addition to intracellular endotoxin. Exotoxin is toxic to mammals including human beings, therefore use of microbial insecticide containing exotoxin is banned in North America, Western Europe and in Japan. Where a strain which does not form exotoxin is used for producing the microbial insecticide, the microbial insecticide containing endotoxin crystals and spores may be employed without further purification for the formulation of the present invention. Where a strain which forms exotoxin is used, it is necessary to remove exotoxin produced during the cultivation. Methods for the removal of exotoxin are well known in the art. The microbial insecticide used in the present invention is accordingly free or substantially free from exotoxin of B.t. Commercially available B.t. products containing crystalline endotoxin and free of exotoxin include Bactospeine ® (product of Biochem Products, a division of Salsbury Laboratories, Inc., Montchanin, Del.) which contains 8800 International Units per milligram (about 1.76% by weight of the active ingredient of *Bacillus thuringiensis* Berliner, var. Kurstaki and Thuricide ® (product of Sandoz, Inc.) which contains 4,000 International Units per milligram (about 0.8% by weight).

The fatty acid for preparing the fatty acid salt (or soap) (b) is selected from oleic acid, linoleic acid, and a mixture thereof. Linolenic acid or ricinoleic acid may also be present in addition to oleic acid and/or linoleic acid. The cation forming the salt or soap with the fatty acid is selected from sodium, potassium and ammonium. Among those, potassium is preferred. Other water-soluble soaps, for example, alkaline earth metal soaps and alkanol-amine salts are also conceivable.

One of the most convenient fatty acid salts is sodium, potassium or ammonium salt of a fatty acid mixture whose main ingredients are oleic acid and linoleic acid, because the acid mixture is easily available and these salts are more soluble in an aqueous medium than others.

In the composition for sale or in the ready-to use composition, the proportions of the active ingredient of the microbial insecticide (a) to the fatty acid salt (b) may range from about 1:1000 to about 1:1 by weight, preferably about 1:500 to about 1:15 by weight. Weight proportions 1:100 to 1:1 or 1:20 to 1:1 are also possible. More preferred proportions are from about 1:350 to 1:20.

The composition for sale may be in any suitable form. Preferred forms include liquid suspensions, (i.e., flowable concentrates), wettable powders and dry dusts. Ingredients required to form these formulations are well known in the art. In the composition for sale the total amount of the microbial insecticide (a) and the fatty acid (b) may vary within a wide range. Practically the amount ranges from 1 to 95, preferably from 5 to 50% by wt. The ready-to-use composition may be in the form of a solution, emulsion or dispersion in suitable solvent. In one preferred embodiment an aqueous solution or dispersion is used in which the concentration of the active ingredient of insecticide (a) ranges from about 0.0001% to 0.1% (preferably 0.001 to 0.02%) by weight and the concentration of fatty acid salt (b) ranges from about 0.05 to about 5 (preferably from about 0.25 to about 2%) by weight.

The ready-to-use composition may be applied to the insects directly or to habitat thereof, for example to plants, to soil, to water in which the insects are expected to occur. One particularly preferred embodiment of the method is to apply an aqueous ready-to-use solution or dispersion containing the essential ingredients of the present invention to plant surfaces on which the insects occur or expected to occur.

It has now been found that when oleic acid is combined with B.t., this fatty acid lowers the insecticidal activity of B.t., at least where the insect is eastern spruce budworm. *Choristoneura fumiferana*, larva., in spite of the fact that oleic acid itself is known to be toxic to some insects.

The invention includes enhanced and synergistic activity from the combination of insecticidal bacterium (a) with the fatty acid (b).

The following examples are illustrative.

EXAMPLE 1

Test of unsaturated $C_{18}$ potassium salt A (oleate/linoleate = 54.0%:43.0%, the balance being other fatty acids) in combination with the microbial insecticide, *Bacillus thuringiensis* Berliner for the control of the western spruce budworm, *Choristoneura occidentalis* Freeman.

Host plant

Douglas-fir, *Pseudotsuga menziesii* (Mirb.)

Sample Unit and Procedure

Western spruce budworm larvae, *Choristoneura occidentalis* Freeman in the 5th and 6th instars were separated into groups containing five larvae per replicate, 5 replicates per treatment and randomly assigned to the following treatments:

(a) Tap water Control (=diluent for treatments)
(b) 0.25% Salt A
(c) 0.1% Bactospeine ® (=0.00176% ai or 1 ml/(of 8.8 cc International Units, B.t. per milligram [1.71% ai]).
(d) 0.3% Thuricide ® International Units of B.t. per milligram [0.8% ai]).
(e) 0.25% Salt A + 0.1% Bactospeine ®*
(f) 0.25% Salt A + 0.3% 12 BU Thuricide ®*

*Both formulations of *Bacillus thuringiensis* Berliner were used at ½ of the recommended label rates.

These solutions were made up fresh before use. The unsaturated fatty acid salts were made by neutralizing a fatty acid mixture of oleic and linoleic (54.0%:43.0%) with potassium hydroxide. The *Bacillus thuringiensis* (B.t.) were two standard retail formulations; Bactospeine ® produced by Salsbury Laboratories Inc. and Thuricide ® produced by Sandoz Inc.

Caged (20×20×24 cm) larvae and foliage (Douglas-fir) were sprayed with 25 ml of treatment solution applied with a 10 ml plastic syringe with a furnace-burner-tip nozzle (Monarch 0.75 GPH; 45°AR). Mortality was assessed by counting living and dead larvae 3 and 10 days after treatment.

Results

Table 1: Observed and corrected mean percent mortality (assessed 10 days post-treatment) of W. spruce budworm, *Choristoneura occidentialis* Freeman to the treatment solutions, and comparison of means between expected additive values with observed values.

| Treatment | Observed Mean % Mort. | Abbotts Corrected Mean % Mort. | Expected Additive Values |
|---|---|---|---|
| Tap water control (= diluent) | 32.0 | 0 | |
| 0.25% Salt A | 40.0 | 11.8 | |
| 0.1% Bactospeine ® (B.t.) | 79.2 | 69.4 | |
| 0.3% Thuricide ® (B.t.) | 75.0 | 63.2 | |
| 0.25% Salt A + 0.1% Bactospeine ® | 96.0 | 94.1 | 81.2 |
| 0.25% Salt A + 0.3% Thuricide ® | 85.7 | 79.0 | 75.0 |

The synergistic interaction of Salt A with the B.t. is clearly evident by referring to the data listed in Table 1. The salt A/B.t. combination gave higher mortality than the sum of the mortalities obtained for salt A or B.t. alone, thus they acted synergistically. These combinations (0.25% Salt A+0.1% Bactospeine ®; and 0.25% Salt A+0.3% Thuricide ®) provided good control of W. spruce budworm larvae at one-half of the recommended rate of the B.t. alone.

In addition to the above described synergistic activity, a reduction in the lag time between treatment and effect was observed in the Salt A/B.t. combinations. Results at the three day post-treatment assessment show enhanced (0.25 Salt A/0.1 Bactospeine ®) and synergistic (0.25% Salt A/0.3% Thuricide ®) activity with respect to budworm mortality in the Salt A/B.t. combinations versus the sum of the Salt A and B.t. mortalities alone (Table 2). Enhanced and synergistic activity at the 3 day post-treatment assessment indicates a reduction in time between treatment and effect in the Salt A/B.t. combinations.

TABLE 2

Observed, corrected and expected additive mean percent mortality of W. spruce budworm, *Choristoneura occidentalis* Freeman 3 days post-treatment.

| Treatment | 3 Day Assessment | | |
|---|---|---|---|
| | Observed Mean % Mort. | Abbott's Corrected Mean % Mort. | Expected Additive Values |
| (a) Tap Water Control (= diluent) | 4.0 | 0 | |
| (b) 0.25% Salt A | 12.5 | 8.9 | |
| (c) 0.1% Bactospeine ® (B.t.) | 39.1 | 36.6 | |
| (d) 0.3% Thuricide ® (B.t.) | 13.6 | 10.0 | |
| (e) 0.25% Salt A + 0.1% Bactospeine ® | 45.8 | 43.5 | 45.5 |
| (f) 0.25% Salt A + 0.3% Thuricide ® | 36.0 | 33.3 | 18.9 |

EXAMPLE 2

Test of unsaturated $C_{18}$ potassium salts (oleate/linoleate=54.0%/43.0% for Salt A and 77%/7% for Salt B, the balance in each case being other fatty acids) in combination with the microbial insecticide, *Bacillus thuringiensis* Berliner for the control of the silverspotted tiger moth, *Halisodota argentata* Packard.

Host Plant
Douglas-fir, *Pseudotsuga menziesii* (Mirb.)

Sample Unit and Procedure

Silverspotted tiger moth larvae (4th and 5th instars) were placed 50 larvae per 1 year old Douglas-fir seedling into cages (23×23×27 cm), with 3 replicates (each containing 50 larvae) per treatment. These were randomly assigned to the following six treatments:

(a) Tap water control (=diluent for treatments)
(b) 0.25% Salt B
(c) 0.25% Salt A
(d) 0.6% Thuricide ® (=0.0048% ai or 6 ml/l Thuricide containing 1000 International Units of B.t. per milligram [0.8% ai]).
(e) 0.25% Salt B+0.6% Thuricide ®
(f) 0.25% Salt A+0.6% Thuricide ®

Approximately 20 mls of fresh treatment solution was applied per replicate to larvae and foliage using a 10 cc plastic syringe with a furnace-burner-tip sprayer (Monarch 0.75 GPH; 45° AR). Mortality was assessed 7 days post-treatment.

TABLE 3

Mortality assessment of silverspotted tiger moth larvae, *Halisidota argentata* Packard to treatment solutions. Assessments made 7 days post-treatment.

| Treatments | Replicates Mort. = X/50 | | | % Mort. | Abbott's Corrected Mort. |
|---|---|---|---|---|---|
| | 1 | 2 | 3 | | |
| (a) Tap water control | 4 | 2 | 6 | 8 | 0 |
| (b) 0.25 Salt B | 35 | 39 | 36 | 73.3 | 71 |
| (c) 0.25 Salt A | 30 | 35 | 31 | 64 | 61 |
| (d) 0.6% Thuricide ® (B.t.) | 20 | 24 | 13 | 38 | 33 |
| (e) 0.25 Salt B + 0.6% Thuricide ® | 40 | 39 | 46 | 83.3 | 81.9 |
| (f) 0.25 Salt A + 0.6% Thuricide ® | 40 | 48 | 44 | 88 | 87 |

Enhanced insecticidal activity was obtained in the Salt B/B.t. (81.9%) and Salt A/B.t. (87.0%) combinations over the mortality obtained from the Salt B (71.0%), Salt A (61%) and B.t. (33%) alone (Table 3).

What we claim as our invention is:

1. An insecticidal composition consisting essentially of:
   (a) An insecticidally effective amount of an entomopathogenic bacterium *Bacillus thuringiensis*-originated insecticide which contains the endotoxin thereof as an active ingredient, is free from the exotoxin thereof, and is insecticidally active against sucking, biting and defoliating insects, and
   (b) a sodium, potassium or ammonium salt of an unsaturated fatty acid having 18 carbon atoms selected from the group consisting of oleic acid, linoleic acid and a mixture thereof in an amount sufficient to be insecticidally effective as well as to synergistically enhance the efficacy of the bacterial insecticide,
   wherein the weight ratio of (a) *Bacillus thuringiensis* (active ingredient:(b) the fatty acid salt is from about 1:1,000 to about 1:1.

2. The composition according to claim 1 wherein the component (b) is potassium salt of the fatty acid.

3. The composition according to claim 1, wherein the component (b) is sodium, potassium or ammonium salt of a fatty acid mixture whose main ingredients are oleic acid and linoleic acid.

4. The composition according to claim 1, wherein the weight ratio of (a) the *Bacillus thuringiensis* (active ingredient):(b) the fatty acid salt ranges from about 1:100 to about 1:1.

5. The composition according to claim 1, wherein the weight ratio of (a) the *Bacillus thuringiensis* (active ingredient):(b) the fatty acid salt ranges from about 1:20 to about 1:1.

6. The composition according to claim 1, wherein the weight ratio of (a) the *Bacillus thuringiensis* (active ingredient):(b) the fatty acid salt ranges from about 1:500 to about 1:15.

7. The composition according to claim 1, wherein the weight ratio of (a) the *Bacillus thuringiensis* (active ingredient):(b) the fatty acid salt ranges from about 1:350 to about 1:20.

8. The composition according to claim 1, wherein the bacterial insecticide is crystalline endotoxin of said bacterium.

9. The composition according to claim 2, wherein the bacterial insecticide is crystalline endotoxin of said bacterium.

10. The composition according to claim 3, wherein the bacterial insecticide is crystalline endotoxin of said bacterium.

11. The composition according to claim 6, wherein the bacterial insecticide is crystalline endotoxin of said bacterium.

12. The composition according to claim 1, which is in the form of an aqueous solution or dispersion in which the concentration of the active ingredient of the insecticide (a) ranges from about 0.0001% to about 0.1% by weight and the concentration of the fatty acid salt (b) ranges from 0.05% to about 5% by weight.

13. The composition according to claim 1, which is in the form of an aqueous solution or dispersion in which the concentration of the active ingredient of the insecticide (a) ranges from about 0.001% to about 0.01% by weight and the concentration of the fatty acid salt (b) ranges from 0.25% to about 2% by weight.

14. The composition according to claim 12 wherein the component (b) is the potassium salt of the fatty acid.

15. The composition according to claim 12, wherein the component (b) is the sodium, potassium or ammonium salt of a fatty acid mixture whose main ingredients are oleic acid and linoleic acid.

16. The composition according to claim 1, wherein the insecticide (a) is crystalline endotoxin of *Bacillus thuringiensis* Berliner, var. Kurstaki.

17. A method of protecting susceptible plants against biting, sucking and defoliating insects, which method comprises
concurrently applying to the insects or habitat thereof both (a) an insecticidally effective amount of an entomopathogenic bacterium *Bacillus thuringiensis*-originated insecticide which contains the endotoxin thereof as an active ingredient, is free from the exotoxin, thereof and is insecticidally active against sucking, biting and defoliating insects, and (b) a sodium, potassium or ammonium salt of an unsaturated fatty acid having 18 carbon atoms selected from the group consisting of oleic acid, linoleic acid and a mixture thereof in an amount sufficient to be insecticidally effective as well as to synergistically enhance the efficacy of the bacterial insecticide, wherein the weight ratio of (a) the *Bacillus thuringiensis* (active ingredient): (b) the fatty acid salt is from about 1:1,000 to about 1:1.

18. The method according to claim 17 wherein the components (a) and (b) are applied together as a composition.

19. The method according to claim 18, wherein the component (b) is the sodium, potassium or ammonium salt of a fatty acid mixture whose main ingredients are oleic acid and linoleic acid.

20. The method according to claim 18, wherein the component (b) is the potassium salt of a fatty acid mixture whose main ingredients are oleic acid and linoleic acid.

21. The method according to claim 18, wherein the composition is in the form of an aqueous solution or dispersion in which the concentration of the active ingredient of the insecticide (a) ranges from about 0.0001% to about 0.1% by weight and the concentration of the fatty acid salt (b) ranges from 0.05% to about 5% by weight.

22. The method according to claim 18, wherein the composition is in the form of an aqueous solution or dispersion in which the concentration of the active ingredient of the insecticide (a) ranges from about 0.001% to about 0.01% by weight and the concentration of the fatty acid salt (b) ranges from 0.05% to about 5% by weight.

23. The method according to claim 21, wherein the weight ratio of (a) the *Bacillus thuringiensis* (active ingredient):(b) the fatty acid salt ranges from about 1:500 to about 1:15.

24. The method according to claim 21, wherein the weight ratio of (a) the *Bacillus thuringiensis* (active ingredient):(b) the fatty acid salt ranges from about 1:350 to about 1:20.

25. The method according to claim 18, wherein the composition is applied to plant surfaces on which the insects occur or are expected to occur.

26. The method according to claim 18, wherein the insect is larvae of western spruce budworm, silverspotted tiger moth.

* * * * *

UNITED STATES PATENT AND TRADEMARK OFFICE
CERTIFICATE OF CORRECTION

PATENT NO. : 4,826,678

DATED : May 2, 1989

INVENTOR(S) : Michelle D. Gaudet et al.

It is certified that error appears in the above-identified patent and that said Letters Patent is hereby corrected as shown below:

Column 4, line 27, change "8.8 cc" to --8,800--.

Column 4, line 28, after "Thuricide ®" insert --(= 0.0024% a.i. or 3ml/l Thuricide ® containing 4000--

Column 5, line 60, change "1000" to --4000--.

Signed and Sealed this

Twenty-second Day of May, 1990

Attest:

HARRY F. MANBECK, JR.

*Attesting Officer*     *Commissioner of Patents and Trademarks*